United States Patent [19]

Toledo-Pereyra

[11] 4,242,883
[45] Jan. 6, 1981

[54] LIVER PRESERVATION

[75] Inventor: Luis H. Toledo-Pereyra, Grosse Pointe Farms, Mich.

[73] Assignee: Henry Ford Hospital, Detroit, Mich.

[21] Appl. No.: 25,774

[22] Filed: Apr. 2, 1979

[51] Int. Cl.³ .............................................. B01F 3/04
[52] U.S. Cl. ........................................ 62/306; 62/78; 62/384; 435/1
[58] Field of Search ...................... 195/1.7; 62/64, 78, 62/306, 384

[56] References Cited

U.S. PATENT DOCUMENTS

| | | | |
|---|---|---|---|
| 3,406,531 | 10/1968 | Swenson et al. | 62/78 |
| 3,545,221 | 12/1970 | Swenson et al. | 62/78 |
| 3,545,225 | 12/1970 | Swenson et al. | 62/78 |
| 3,607,646 | 9/1971 | Roissart | 62/306 |
| 3,753,865 | 8/1973 | Belzer et al. | 62/306 |
| 3,777,507 | 12/1973 | Burton et al. | 62/306 |
| 3,810,367 | 5/1974 | Peterson | 62/64 |
| 3,914,954 | 10/1975 | Doerig | 62/384 |

OTHER PUBLICATIONS

Toledo, L. H. et al., 1975 Ann. Surg. 181: 289-298 Factors Determining Successful Liver Preservation for Transplant.
Toledo, L. H. et al., Forty Eight Hrs. Hypothermic Pulsatile Perfusion of Canine Hearts before Transplantation, Cryobiology 16, 1979, pp. 343-349.
Calne, R. Y. et al., Liver Preservation by Single Passage Hypothermic Squirt Perfusion; British Medical Journal, 1972, 4, pp. 142-144.

Primary Examiner—Ronald C. Capossela
Attorney, Agent, or Firm—Barnes, Kisselle, Raisch & Choate

[57] ABSTRACT

A method and apparatus for perfusing livers comprising a portable container and a liver receptacle removably positioned in such container. Portions of the receptacle are spaced from the walls of the container when the receptacle is in position so that ice may be positioned around the receptacle. A perfusate holder is mounted on the container. A second container surrounds a portion of the holder and is adapted to receive ice. An intermittently operated flow regulator controls gravity flow of perfusate at predetermined rate from the holder to the receptacle and a timer controls operation of controller at predetermined time intervals.

2 Claims, 3 Drawing Figures

U.S. Patent  Jan. 6, 1981  4,242,883
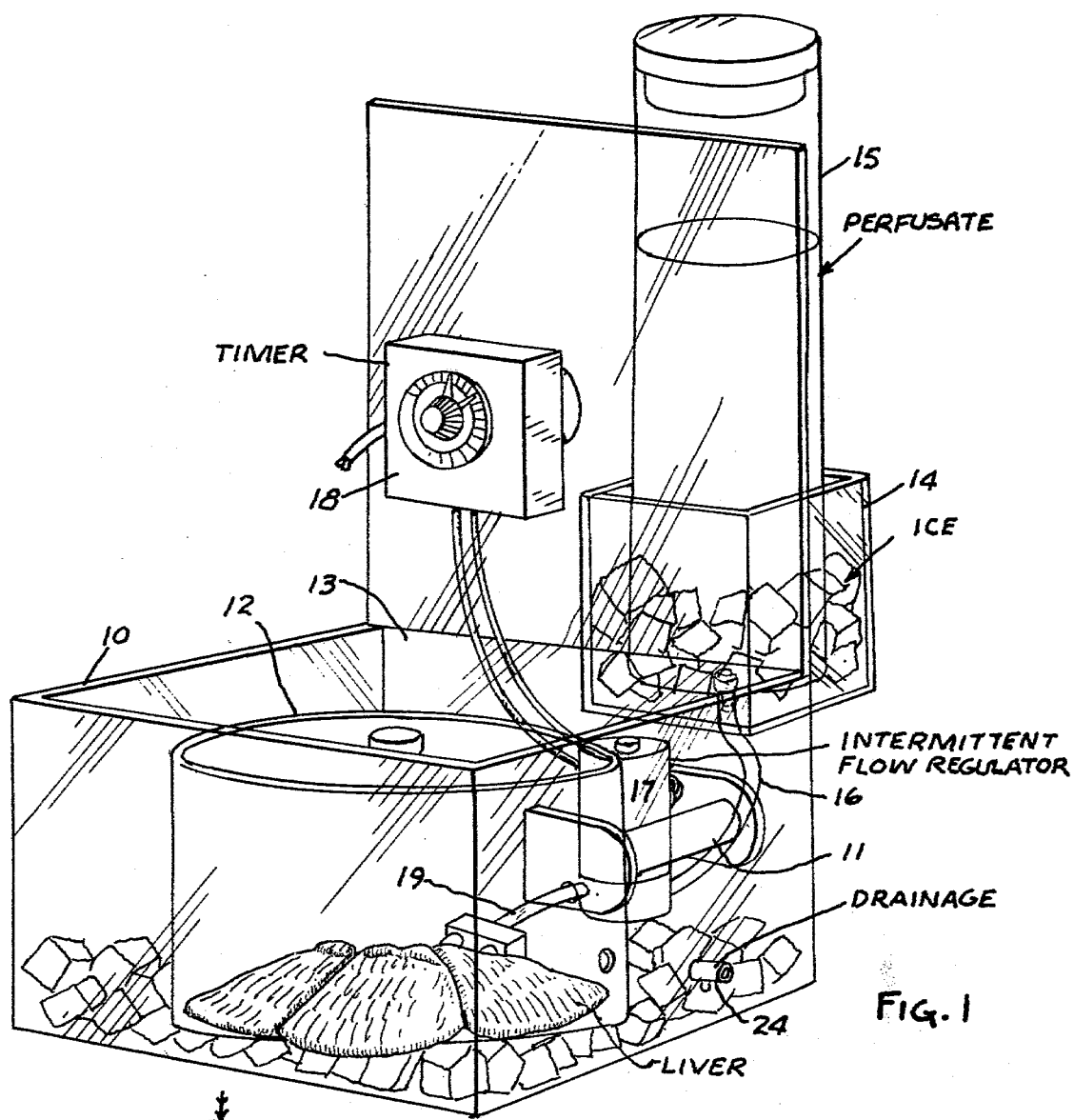
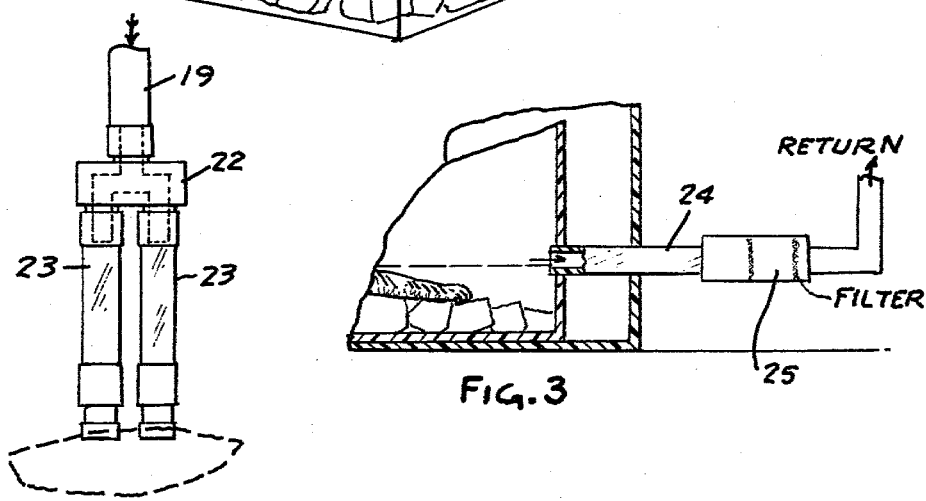

LIVER PRESERVATION

This invention relates to liver preservation for transport and transplant and particularly to liver preservation module.

BACKGROUND AND SUMMARY OF THE INVENTION

Although, several methods of liver preservation for transplantation have been previously used, in general, the results reflect the difficulties in establishing a consistent technique. The variability of the results are related to the type and length of preservation, the chemical characteristics of the perfusate, and the individual response of the liver to hypothermic perservation. Previously, it has been demonstrated that 24 hours of satisfactory liver preservation could be obtained by significant modifications in the perfusate solution. Toledo-Pereyra, L. H., Simmons, R. L. and Najarian, J. S.: 1975. Ann. Surg., 181:289; Toledo-Pereyra, L. H., Chee, M. and Lillehei, R. C.: Cryobiology. Accepted. This study describes a new method for liver hypothermic intermittent perfusion that will provide consistent preservation for 24 hours.

It has been heretofore proposed that porcine livers can be preserved by a single passage, hypothermic intermittent spuirt perfusion for up to 17 hours. Such a system utilizes an apparatus wherein a timer controls a pump to squirt a bolus of perfusate. Calne, R. Y., Dunn, D. C., Herbertson, B. M. et al; 1972. Brit. Med. J., 4:142.

The present invention provides a simpler and more efficient method and apparatus for 24 hour ex-vivo hypothermic intermittent liver perfusion.

DESCRIPTION OF THE DRAWINGS

FIG. 1 is a perspective view of an apparatus embodying the invention.

FIG. 2 is a plan view of a portion of the same.

FIG. 3 is a side sectional view of a modified form of the same.

DESCRIPTION

Referring to FIGS. 1-3, the portable apparatus for performing the liver perfusion comprises a container 10 having handles 11 thereon and a cylindrical organ receptacle 12 positioned in container 10 so that ice can be placed about the receptacle 12. The rear wall 13 of container 10 extends vertically upwardly and supports a smaller rectangular container 14 in which a cylindrical holder 15 for perfusate is positioned. Ice is positioned in container 14 around the lower end of holder 15. Container 10, receptacle 12, container 14 and holder 15 are preferably made of transparent material such as acrylic plastic.

A tube 16 extends from the lower end of holder 15 through a hole in the container 14 to a solenoid operated flow regulator 17 which is controlled by a variable timer 18. A tube 19 extends from the regulator 17 through an opening 20 in the side wall of receptacle 12 to a manifold 22. Tubes 23 in turn extends from manifold 22 to the liver L. A suitable seal can be provided between the hole in the container 14 and the tube 16 extending through the hole.

The size of the holder is such that the perfusate is delivered at a low pressure of 8–10 mmHg. so that the perfusate is delivered at 5–10 ml/min. The timer interval can be varied from 2 to 5 minutes.

The perfusate emanating from the liver can be drained through an outlet 24. If the perfusate is to be recirculated a filter 25 is provided.

EXAMPLE

Adult mongrel dogs of either sex, weighing between 15 to 23 Kgs, were used as donors or recipients for orthotopic liver transplantation. All dogs received sodium thiamylal for induction and fluothane for maintenance (0.5–1.5%). Isoproterenol 0.4mg was given in a continuous intravenous infusion over two hours starting one hour before liver excision, and methylprednisolone 30 mg/K was given two hours before removal. Immediately before vascular clamping, 2,000 U of sodium herapin was administered intravenously.

After the donor's liver had been excised, it was placed in the liver preservation device, (LH-1) (FIG. 1) which basically consists of a low pressure, intermittent flow system that delivers the perfusate to the organ in a sequential time span (every 2 to 5 min.). The temperature was kept at 4° C. with ice, or the entire apparatus was placed in a refrigerator (4–7° C.) for the remaining period to complete 24 hours. During perfusion, osmolarity, electrolytes, blood gases, and lactic acid were determined every two hours and then every 8 hours until the end of perfusion. The liver was weighed before and at the end of the study, and after perfusion it was transplanted orthotopically.

All recipient dogs were given intravenous Ringer's lactate with dextrose 5% and potassium chloride (20 mEq/L) for several days until oral diet started. All dogs were treated with azathioprine 5 mg/K/day for three days and then 2.5 mg/K/day until death. Blood samples were obtained daily for two weeks and twice a week thereafter for hemoglobin, hematocrit, WBC, electrolytes, lactic acid, bilirubin alkaline phosphatase and glutamic piruvic transaminase. Postmortem examination was performed on all animals. Biopsies from the liver were obtained immediately after transplantation and at the time of death. Statistical analysis with standard errors and Student's t-test were determined for all parameters.

Twelve animals were divided in two groups. Group I (n=6) received livers which had been perfused with Collins' solution containing in 1 L $K_2HPO_4$ (7.4 gm), $KH_2PO_4$ (2.0 gm), KCl (1.1 gm), $NaHCO_3$ (0.8 gm), $MgSO_4$ (50%) (14 ml), dextrose (50%) (50 ml), herapin (10 ml). Group II dogs (n=6) received livers that had been perfused with an albuminplasmanate solution which contained in 1 L PPF (750 ml), dextrose (50%) (2 ml), $MgSO_4$ (50%) (2 ml), KCl (4 mEq), $NaHCO_3$ (8 ml), and albumin (12,5 gm). Both perfusates contained ampicillin (500 mg/L), insulin (40 U/L) and methylprednisolone (500 mg/L). There were no animal exclusions in this study.

Table I shows that preservation, clinical characteristics, and cause of death for all animals. Livers used in both groups were given similar rates of flow and perfusion pressure. No significant differences in weight gain (p 0.08) were noted. The osmolarity, electrolytes, and the lactic acid did not change significantly (p 0.8) from control valves. In the Collins' group, the pH varied from 7.15 to 7.21 and in the colloid group it remained at 7.35. Although no dogs in the Collins' group survived for as long as one day, there were several long-term survivors in the colloid group.

In these long-term survivors, the liver function tests showed normal implantation response within three days. Ten days to two weeks later the serum bilirubin and alkaline phosphatase increased progressively until death. Histology correlated well with the immediate functional response after liver transplantation. Well-preserved livers had a normal histological image, while those that were not had moderate to severe degrees of necrosis, portal hemorrhage, cellular infiltration and edema.

These initial experiments indicate that it is possible to preserve the liver with a colloid solution under hypothermic intermittent perfusion without oxygenation for 24 hours. Calne and his group, referred to above used a system somewhat similar to ours to perfuse pig livers for 12 to 17½ hours before orthotopic transplantation. The livers were perfused with plasma protein fraction which contained in 1 L: 15 mEq of $K_2HPO_4$, 250 mg of dextrose, 5 ml of $MgSO_4$ (10%), 250 mg of hydrocortisone, 500 mg of ampicillin, and n/10 HCl to lower the pH to 6.8. Among the advantages of the present system are that it does not require filters, oxygenation or a cooling coil. In addition, the perfusate can be re-circulated, and the liver is subjected to less pressure and perfusate fluid. A lighter, simpler and more portable unit is thus readily available for transplantation. There were no technical failures, or any problems associated with air emboli or other technical perfusion faults. This system thus is a good alternative to other systems that have been experimentally or clinically used for liver preservation and is feasible and reproducible for preserving livers for 24 hours when appropriate preservation solutions are used with good functional response after orthotopic allografting.

| Dog No. | Flow (ml/min) | Perfusion Pressure (mmHg) | Weight Gain (%) | Perfusate | Survival | Cause of Death |
| --- | --- | --- | --- | --- | --- | --- |
| 1. | 10 | 8-10 | 12.3 | Collins | 8 hours | Hemorrhage |
| 2. | 10 | 8-10 | 17.8 | Collins | 2 hours | Split liver and hemorrhage |
| 3. | 5 | 8-10 | 8.7 | Collins | 4 hours | Acute portal vein occlusion |
| 4. | 10 | 8-10 | −1.7 | Collins | 6 hours | Hepatic Necrosis |
| 5. | 5 | 8-10 | −0.3 | Collins | 6 hours | Split liver and hemorrhage |
| 6. | 10 | 8-10 | 18.3 | Collins | 12 hours | Portal vein and hepatic artery thrombosis |
| 7. | 10 | 8-10 | 7.3 | Albumin/Plasmanate | 27 days | Intussusception and peritonitis rejection |
| 8. | 10 | 8-10 | 5.8 | Albumin/Plasmanate | 21 days | Liver failure |
| 9. | 5 | 8-10 | 6.2 | Albumin/Plasmanate | 14 days | Rejection and liver failure |
| 10. | 5 | 8-10 | 3.1 | Albumin/Plasmanate | 5 days | Septicemia |
| 11. | 5 | 8-10 | −6.7 | Albumin/Plasmanate | 9 days | Peritonitis |
| 12. | 10 | 8-10 | −1.8 | Albumin/Plasmanate | 10 days | Late portal vein thrombosis |

I claim:
1. An apparatus for perfusing livers comprising
a portable container,
a liver receptacle removably positioned in such container,
portions of said receptacle being spaced from the walls of said container when the receptacle is in position so that ice may be positioned around the receptacle,
a perfusate holder mounted on said container for containing perfusate at ambient pressure,
a second container surrounding a portion of said holder and adapted to receive ice,
an intermittently operated flow regulator for controlling flow of perfusate solely by gravity from said holder to said receptacle,
a timer for controlling operation of said controller,
said receptacle having an outlet.
2. The apparatus set forth in claim 1 including handles on said receptacle.

* * * * *